US010351884B2

(12) United States Patent
Otero Casal et al.

(10) Patent No.: US 10,351,884 B2
(45) Date of Patent: Jul. 16, 2019

(54) METHOD FOR THE ENRICHMENT OF MICROALGAE BIOMASS IN POLYUNSATURATED FATTY ACIDS

(71) Applicants: ALGAENERGY, S.A., Alcobendas (ES); UNIVERSIDADE DE SANTIAGO DE COMPOSTELA, Santiago de Compostela (ES)

(72) Inventors: Ana María Otero Casal, Santiago de Compostela (ES); Isabel Freire Fontáns, Santiago de Compostela (ES); Hugo Alexandre Milhazes Da Cunha, Santiago de Compostela (ES); María Segura Fornieles, Alcobendas (ES); Juan Pablo Jiménez Martín, Alcobendas (ES)

(73) Assignees: ALGAENERGY, S.A., Alcobendas (Madrid) (ES); UNIVERSIDADE DE SANTIAGO DE COMPOSTELA, A Coruña (ES)

( * ) Notice: Subject to any disclaimer, the term of this patent is extended or adjusted under 35 U.S.C. 154(b) by 72 days.

(21) Appl. No.: 15/515,718

(22) PCT Filed: Oct. 15, 2014

(86) PCT No.: PCT/ES2014/070780
§ 371 (c)(1),
(2) Date: Mar. 30, 2017

(87) PCT Pub. No.: WO2016/059262
PCT Pub. Date: Apr. 21, 2016

(65) Prior Publication Data
US 2017/0306364 A1   Oct. 26, 2017

(51) Int. Cl.
| *C12P 7/64* | (2006.01) |
| *C12N 1/12* | (2006.01) |
| *C12P 13/04* | (2006.01) |
| *C12P 23/00* | (2006.01) |
| *C12P 21/00* | (2006.01) |

(52) U.S. Cl.
CPC .............. *C12P 7/6427* (2013.01); *C12N 1/12* (2013.01); *C12P 13/04* (2013.01); *C12P 23/00* (2013.01); *C12P 21/00* (2013.01)

(58) Field of Classification Search
None
See application file for complete search history.

(56) References Cited

U.S. PATENT DOCUMENTS

2004/0009160 A1   1/2004   Villamar et al.

FOREIGN PATENT DOCUMENTS

| CN | 103627623 A | 12/2014 |
| JP | S62239981 A | 10/1987 |
| JP | H09252761 A | 9/1997 |
| WO | 2014146098 A1 | 9/2014 |
| WO | 2016059262 A1 | 4/2016 |

OTHER PUBLICATIONS

Babuskin. Cookies and Pasta with Marine Microalga, Food Technol. Biotechnol. 52 (3) 292-299 (2014).*
Sanchez-Torres H et al.: "Produccion De La Microalga *Nannochloropsis oculata* (Droop) Hibberd En Medios Enriquecidos Con Ensilado Biologico De Pescado", Ecologica Aplicada, 2008, vol. 7 (1, 2), pp. 149-158. ISSN 1726-2216. The whole document.
Fredriksson Sofia et al. "Fatty acid and carotenoid composition of egg yolk as an effect of microalgae addition to feed formula for laying hens." Food Chemistry 2006 vol. 99, No. 3. pp. 530-537. ISSN 0308-8146. The whole document.
Camacho-Rodriguez J et al. "A low-cost culture medium for the production of Nannochloropss gaditana biomass optimized for aquaculture", Bioresource Technology, (2013), vol. 144, pp. 57-66 <http://dx.doi.org/10.1016/j.biortech.2013.06.083>.
Gonzalez-Lopez CV et al.: "Medium recycling for Nannochloropsis gaditana cultures for aquaculture", Bioresource Technology, (2013), vol. 129, pp. 430-438 <http://dx.doi.org/10.1016/j.biortech.2012.11.061>.
Ferreira, M et al. "Enriching Rotifers with "Premium" Microalgae *Nannochloropsis gaditana*." Mar. Biotechnol 2009, vol. 11, pp. 585-595.
Spanish Patent Office, International Search Report for PCT Application No. PCT/ES2014/070780 dated Oct. 6, 2015.
Spanish Patent Office, Written Opinion of the International Search Authority for PCT Application No. PCT/ES2014/070780 dated Jun. 9, 2015.
Ahn, Y.J., Kim, G.J., Kim, J.E., Kim, Y.H., Ko, M.S. Yun, S.Y. 2005. Process for producing Chlorella containing omega-3 fatty acids including eicosapentaenoic acid (EPA) and docosahexaenoic acid (DHA), comprises adding EPA and DHA monoglycerides to the culture medium at the end of fermentation. KR2005015233-A; KR768757-B1.

(Continued)

*Primary Examiner* — Yong D Pak
(74) *Attorney, Agent, or Firm* — SoCal IP Law Group LLP; Nikki M. Dossman (57) ABSTRACT

Process for enriching microalgal biomass, in particular of the genus *Nannochloropsis*, with different polyunsaturated fatty acids, primarily docosahexaenoic acid (22:6 n-3, DHA), using oils that are rich in these fatty acids. The process comprises the following steps:
Preparing a solution or an emulsion of lipids+emulsifying agent (BSA),
Preparing the biomass concentrate to obtain a final concentration of mg/ml or greater,
Enriching the biomass concentrate by adding the lipids or the emulsion thereof to the microalgal concentrate,
Allowing the mixture to rest under constant stirring for at least 24 hours under lighting conditions.
The process allows for the simultaneous enrichment of microalgal biomass of the genus *Nannochloropsis* with eicosapentaenoic acid (20:5 n-3) (EPA) and docosahexaenoic acid (22:6 n-3) (DHA), to obtain a minimum EPA:DHA weight ratio of 10:1, with an EPA content of at least 10% of the total fatty acid content.

7 Claims, 5 Drawing Sheets

(56) References Cited

OTHER PUBLICATIONS

Aragão, C., Conceição, L.E.C., Dinis, M.T., Fyhn, H.-J. 2004. Amino acid pools of rotifers and Artemia under different conditions: nutritional implications for fish larvae. Aquaculture 234: 429-445.

Basen, T., Rothhaupt, K-O., Martin-Creuzburg, D. 2012. Absence of sterols constrains food quality of cyanobacteria for an invasive freshwater bivalve. Oecologia 170:57-64.

Bentley, C.D., Carroll, P.M., Watanabe, W.O. 2008. Intensive rotifer culture in a pilot-scale continuous recirculating system using non-viable microalgae and an ammonia neutralizer. J World Aquac Soc 39:625-635.

Bligh, E.G., Dyer, W.J. 1959. A rapid method of total lipid extraction and purification. Can J Biochem Physiol 37: 911-917.

Chini Zittelli, G. Lavista, F., Bastianini, A., Rodolfi, L., Vincenzini, M., Tredici, M.R. 1999. Production of eicosapentaenoic acid by *Nannochloropsis* sp. cultures in outdoor tubular photobioreactors. Journal of Biotechnology 70: 299-312.

Chlorella Kogyo Co. Ltd. 1999. Production of Chlorella containing highly unsaturated fatty acids—comprises culture of Chlorella in medium containing DHA and other highly unsaturated fatty acids in free acid or salt form. JP10276684-A; KR98080312-A; JP3096654-B2; KR428732-B; KR423876-B.

Doan, T.T.Y., Sivaloganathan, B., Obbard, J.P. 2011. Screening of marine microalgae for biodiesel feedstock. Biomass and Bioenergy 35: 2534-2544.

Freire, I,. Cortina, A., Barreiro, P., Llamas B., Otero, A. 2013. Nannochloropsis limnetica: a new freshwater microalgal species for marine aquaculture. Aquaculture Conference 2013: Celebrating 40 Years of Aquaculture—Nov. 2013, Gran Canaria (Spain).

Patente Gladue, R.M., Behrens, P.W. 2002. DHA-containing nutritional compositions and methods for their production. US 6372460B1.

Hayashi, M., Yukino, T., Maruyama, I., Kido, S., Kitaoka, S. 2001. Uptake and accumulation of exogenous docosahexaenoic acid by Chlorella. Biosci. Biotechnol. Biochem. 65:202-204.

Hibberd, D.J. 1981. Notes of the taxonomy and nomenclatures of the algal clases Eustigmatophyceae and Trbophyceae (synom Xanthophyceae). Bot J Linnean Society 82:93-119.

Hibberd, D.J., Leedale, G.F. 1972. Observations on the cytology and ultrastructure of the new algal class, Eustigmatophyceae. Annals of Botany 36:49-71.

Hirayama, K., Nakamura, K. 1976. Fundamental studies on the physiology of rotifers in mass culture—V. Dry Chlorella powder as a food for rotifers. Aquaculture 8:301-307.

Izquierdo, M.S. 1996. Essential fatty acid requirements of cultured marine fish larvae. Aquaculture Nutrition, 2: 183-191.

Jeffrey, S.W., Vesk, M. 1997. Introduction to marine phytoplankton and their pigment signatures. In: Phytoplankton pigments in oceanography. S.W. Jeffrey, R.F.C. Mantoura, S.W. Wright (Eds.). UNESCO Publishing Paris, pp. 37-84.

Kobayashi, T., Nagase, T., Hino, A., Takeuchi, T. 2008. Effect of combination feeding of Nannochloropsis and freshwater Chlorella on the fatty acid composition of rotifer Brachionus plicatilis in a continuous culture. Fisheries Sci 74:649-656.

Koiso, M., Yoshikawa, M., Kuwada, H., Hagiwara, A. 2009. Effect of maternal diet on survival and life history parameters of next generations in the rotifers *Brachionus plicatilis* sp. complex. Nippon Suisan Gakk 75:828-833.

Krienitz, L., Hepperle, D., Stich, H.-B. Weiler, W. 2000. Nannochloropsis limnetica (Eustigmatophyceae), a new species of picoplankton from freshwater Phycologia 39:219-227.

Krienitz, L., Manfred, W. 2006. The high content of polyunsaturated fatty acids in Nannochloropsis limnetica (Eustigmatophyceae) and its implication for food web interactions, freshwater aquacultulture and biotechnology. Limnologia 36:204-210.

Lubian, L.M., Establier, R. 1982. Estudio comparativo de la composición de pigmentos de varias cepas de Nannochloropsis (Eustigmatophyceae). Investigación Pesquera 46:379-389.

Luzbens, E., Gibson, O., Zmora, O., Sukenik, A. 1995. Potential advantages of frozen algae (*Nannochloropsis* sp.) for rotifer (Brachionus plicatilis) culture. Aquaculture 133:295-309.

Maruyama, I., Nakamura, T., Matsubayashi, T., Ando, Y., Maeda, T. 1986. Identification of the alga known as "marine Chlorella" as a member of the Eustigmatophyceae. Jap. J. Phycol. 34:319-325.

Maruyama, I., Ando, Y., Maeda, T., Hirayama, K. 1989. Uptake of vitamin B12 by various strains of unicellular algae *Chlorella*. Nippon Suisan Gakkaishi 55:1785-1790.

Maruyama, I., Hirayama, K. 1993. The culture of the rotifer Brachionus plicatilis with Chlorella vulgaris containing Vitamin B12 in its cells. Journal of the World Aquaculture Society 24:194-198.

Maruyama, I., Nakao, I., Shigueno, Y., Ando, Y., Hirayama, K. 1997. Application of unicellular algae *Chlorella vulgaris* for the mass culture of marine rotifer Brachionus. Hydrobiologia 358: 133-138.

Mendes, A., Reis, A., Vasconcelos, R., Guerra, P., Lopes da Silva, T. 2008. Cryptecodinium cohnii with emphasis on DHA production: a review. Journal of Applied Phycology 21:199-214.

Müller-Navarra, D.C., Brett, M.T., Liston, A.M., and Goldman, C.R. 2000. A highly unsaturated fatty acid predicts carbon transfer between primary producers and consumers. Nature 403:74-77.

Nuria Navarro, N., Yúfera, M., García-Gallego, M. 2001. Use of freeze-dried microalgae for rearing gilthead seabream, *Sparus aurata* L., larvae. II. Biochemical composition. Hydrobiologia 452: 69-77.

Rodolfi L., Chini Zitelli, G., Bassi, N., Padovani, G., Biondi, N., Bonini, G., Tredici, M.R. 2008. Microalgae for oil: strain selection, induction of lipids synthesis and outdoor mass cultivation in a low-cost photobioreactor. Biotechnol Bioeng 102:100-112.

San Pedro, A., González-López, C.V., Acién, F.G., Molina-Grima, E. 2013. Marine microalgae selection and culture ,conditions optimization for biodiesel production. Bioresource Technology 134:353-361.

Santos, L.M. 1996. The Eustigmatophyceae: actual knowledge and research perspectives. Beiheft Nova Hedwigia 112:391-405.

Sato N., Murata. 1988. Membrane lipids. In: Packer L., Glazer A.N. (Eds.). Methods Enzimol. vol. 167. Academic Press, New York, 251-259.

Siriwardhana, N., Kalupahana, N.S., Moustaid-Moussa, N. 2012. Health Benefits of n-3 Polyunsaturated Fatty Acids: Eicosapentaenoic Acid and Docosahexaenoic Acid, In: Se-Kwon Kim (Ed.), Advances in Food and Nutrition Research, Academic Press, 2012, vol. 65, pp. 211-222.

Srivastava, A., Hamre, K., Stoss, J., Chakrabarti, R., Tonheim, S.K. 2006. Protein content and amino acid composition of the live feed rotifer (Brachionus plicatilis): with emphasis on the water soluble fraction. Aquaculture 254:534-543.

Sugimoto, Y., Taga, C., Nishiga, M., Fujiwara, M., Konishi, F., Tanaka, K., Kamei, C. 2002. Effect of docosahexaenoic acid-fortified Chlorella vulgaris strain CK22 on the radial maze performance in aged mice. Biol. Pharm. Bull 25:1090-1092.

Sukenik, A. 1999. Production of eicosapentaenoic acid by the marine eustigmatophyte *Nannochloropsis* sp. In: Cohen, Z. (Ed.), Chemicals from Microalgae. Taylor and Francis, London, p. 41-56.

Sukenik, A., Zmora, O., Carmeli, Y. 1993. Biochemical quality of marine unicellular algae with special emphasis on lipid composition. II. *Nannochloropsis* sp. Aquaculture 117:313-326.

Tocher, D.R. 2010. Fatty acid requirements on ontonegy of marine and freshwater fish. Aquaculture research 41:717-732.

Volkman, J.K., Jeffrey, S.W., Nichols, P.D., Rogers, G.I., Garland, C.D. 1989. Fatty acid and lipid composition of 10 species of (56) References Cited

OTHER PUBLICATIONS microalgae used in mariculture. Journal of Experimental Marine Biology and Ecology, 128: 219-240.

Wacker, A., Becher, P., von Elert, E. 2002. Food quality effects of unsaturated fatty acids on larvae of the zebra mussel *Dreissena polymorph*. Limnol. Oceanogr. 47:1242-1248.

Wacker, A., Martin-Creuzburg, M. 2007. Allocation of essential lipids in Daphnia magna during exposure to poor food quality. Functional ecology 21:738-747.

Wacker, A., von Elert, E. 2003. Food quality controls reproduction of the zebra mussel (*Dreissena polymorpha*). Oecologia 135:332-338.

Watanabe, T., Kitayama, C., Fujita, S. 1983. Nutritional values of live organisms used in Japan for mass propagation of fish: a review. Aquaculture 34:115-143.

Whittle, S.J., Casselton, P.J. 1975. The chloroplast pigments of the algal classes Eustigmatophyceae and Xantophyceae. I. Eustigmatophyceae. British Phycological Journal 10:179-191.

Yoshimura, K., Tanaka, K., Yoshimatsu, T. 2003. A novel culture system for the ultra-high-density production of the rotifer, Brachionus rotundiformis—a preliminary report. Aquaculture 227:165-172.

\* cited by examiner

METHOD FOR THE ENRICHMENT OF MICROALGAE BIOMASS IN POLYUNSATURATED FATTY ACIDS

SECTOR OF THE INVENTION

The present invention relates to a process for enriching microalgal biomass with long-chain polyunsaturated fatty acids. More specifically, it relates to microalgae of the genus *Nannochloropsis*. It also relates to the products obtained by means of this process and the uses thereof.

BACKGROUND OF THE INVENTION

The species of the genus *Nannochloropsis* belong to the Division Eustigmatophyta, Class Eustigmatophyceae, Order Eustigmatales, Family Monodopsidaceae (Hibberd, 1981, Bot J Linnean Society 82:93-119). The class was separated from the Xanthophyceae on the basis of its structure and cytology, and, subsequently, due to its pigment composition, since it lacks chlorophyll b (Hibberd & Leedale, 1972, Annals of Botany 36:49-71; Whittle & Casselton, 1975, British Phycological Journal 10:179-191).

*Nannochloropsis* cells are coccoid cells, with an approximate diameter of 2-4 µm, they do not have flagella and do not present moving states. They have a green-yellow colour, and for this reason may be confused with Chlorophyta cells (Santos, 1996, Beiheft Nova Hedwigia 112:391-405), which has led various publications to designate the *Nannochloropsis* species as marine *Chlorella* (Maruyama et al., 1986, Jap. J. Phycol. 34:319-325; Watanabe et al., 1983, Aquaculture 34:115-143). Apart from the morphological differences and the differences in pigment composition, since Chlorophyta present chlorophylls a and b, whereas Eustigmatophyceae only present chlorophyll a, in addition to various carotenoids, which may be used as a taxonomic character (Jeffrey & Vesk, 1997, Phytoplankton pigments in oceanography, S. W. Jeffrey, R. F. C. Mantoura, S. W. Wright (Eds). UNESCO Publishing Paris, pp 37-84; Lubian & Establier, 1982, Investigación Pesquera 46:379-389), both groups present significant differences in their fatty acid profile, since, whereas chlorophytes do not contain fatty acids with more than 18 carbon atoms, species of the genus *Nannochloropsis* present a high percentage of the omega-3 polyunsaturated fatty acid eicosapentaenoic (20:5 n-3, EPA) (Ferreira et al., 2009, March Biotechnol 11:585-595; Sukenik et al., 1993, Cohen, Z. (Ed.), Chemicals from Microalgae. Taylor and Francis, London, p 41-56), which may represent up to 25% of the fatty acids in this group and which, in addition to being essential for application in aquaculture, has various functional properties in animals and humans (Siriwardhana et al., 2012, Se-Kwon Kim, (Eds), Advances in Food and Nutrition Research, Academic Press, 2012, Volume 65, Pages 211-222); this makes this genus important from the biotechnological and pharmacological standpoints. Most of the species described belong to marine or brackish habitats, and the first freshwater species, *Nannochloropsis limnetica*, was described in 2000 (Krienitz et al., 2000, Phycologia 39:219-227). The fatty acid composition of *N. limnetica* is similar to that of the marine species, with an EPA content that may be as high as 24% of the total fatty acid content (Freire et al., 2013, Aquaculture Conference 2013: Celebrating 40 Years of Aquaculture—November, 2013, Gran Canaria (Spain); Krienitz et al., 2006, Phycologia 39:219-227).

Various marine species of the genus *Nannochloropsis* are cultured all over the world, to be used in the live food chain for the larval culture of marine fish, and are amongst the most commonly used species in mariculture. The main application of the marine species of the genus *Nannochloropsis* is in the culture of rotifers of the genus *Brachionus*, which are used as live food for marine fish larvae. Rotifer culture is a process that requires high quantities of microalgae, since these represent the only diet that allows for sustained, stable production under continuous culture, with high densities (Yoshimura et al., 2003, Aquaculture 227:165-172; Bentley et al., 2008, J World Aquac Soc 39:625-635). Moreover, microalgae of the genus *Nannochloropsis* result in a better growth and biochemical composition of the rotifers than the yeast *Saccharomyces cerevisiae*, which may also be used as food for rotifers (Luzbens et al., 1995, Aquaculture 133:295-309), or other artificial diets (Aragão et al., 2004, Aquaculture 234:429-445; Srivastava et al., 2006, Aquaculture 254:534-543; Koiso et al., 2009, Nippon Suisan Gakk 75:828-833). The high content of long-chain polyunsaturated fatty acids (PUFAs), especially EPA, in the species of the genus *Nannochloropsis* has been identified as the reason for its high nutritional value in aquaculture, both in the case of the rotifer *Brachionus plicatilis* fed with marine species of this genus (Watanabe et al., 1983, Aquaculture 34:115-143), and in the case of the zebra mussel (*Dreissena polymorpha*), the water flea *Daphnia magna* or the freshwater clam *Corbicula fluminea* fed with the freshwater species *Nannochloropsis limnetica* (Wacker & von Elert, 2003, Oecologia 135:332-338; Wacker et al., 2002, Limnol. Oceanogr. 47:1242-1248; Basen et al., 2012, Oecologia 170:57-64; Wacker & Martin-Creuzburg, 2007, Functional Ecology 21:738-747). Recently, it has been disclosed that the freshwater species *Nannochloropsis limnetica* may be used in the culture of *Brachionus plicatilis* in sea water with excellent results (Freire et al., 2013, Aquaculture Conference 2013: Celebrating 40 Years of Aquaculture—November, 2013, Gran Canaria (Spain)).

Concentrates of the freshwater microalga *Chlorella* are also being successfully used to maintain dense cultures of the rotifer *Brachionus* sp., although the marine species of the genus *Nannochloropsis* produce similar or higher growth rates (Hirayama & Nakamura, 1976, Aquaculture 8:301-307; Maruyama et al., 1997; Kobayashi et al., 2008). Since the *Chlorella* biomass industrially produced under mixotrophic or heterotrophic conditions is deficient in vitamin B12, which is essential for the growth of rotifers, the commercial products of this freshwater microalga designed to be used in aquaculture are enriched with this vitamin, which, in general, is directly added to the culture medium (Maruyama et al., 1989, Nippon Suisan Gakkaishi 55:1785-1790; Maruyama & Hirayama, 1993, Journal of the World Aquaculture Society 24:194-198). In the case of the marine species of *Nannochloropsis*, which are autotrophically cultured, the addition of this vitamin to the culture medium or subsequent enrichment with it are not necessary to obtain maximum rotifer growth rates. Moreover, the main advantage of *Nannochloropsis* species over other species of unicellular algae, more specifically, over species of *Chlorella*, is their high Eicosapentaenoic acid (EPA, 20:5 (n-3)) content, absent in species of the genus *Chlorella*, which is essential for the development of the fish larvae and is transferred to them through the rotifers. Currently, there are various commercial refrigerated, frozen, condensed or lyophilised products based on marine species of *Nannochloropsis* which produce good results for rotifer growth (Luzbens et al., 1995, Aquaculture 133:295-309; Navarro et al., 2001, Hydrobiologia 452:69-77). These products compete with a commercial product called *Chlorella* SV-12 (Pacific Trading Co., Ltd., *Chlorella* Industry Co., Ltd. http://www- .pacific-trading.co.jp/en/product/01-2.html), which is a *Chlorella* concentrate (approx. 13.5% dry weight) artificially enriched to contain 17% of the long-chain fatty acid docosahexaenoic acid (22:6 (n-3), DHA). As reported by the attached technical specifications of the product, this biomass contains only 2% EPA (EPA:DHA ratio, 1:8.5).

The process for enriching *Chlorella* with DHA has been previously disclosed for use in the culture of rotifers (Hayashi et al., 2001, Biosci. Biotechnol. Biochem. 65:202-204). *Chlorella* cells were heterotrophically cultured with glucose, and tuna oil (0.5%) containing 26.8% DHA or free fatty acids obtained from the hydrolysate of the same oil was added for 24 hours. These authors were not able to obtain enrichment using oils, and it was only possible to enrich different species of *Chlorella* by using free fatty acids, to 16.9% of the total fatty acid content (Hayashi et al., 2001, Biosci. Biotechnol. Biochem. 65:202-204), as the use of non-hydrolysed oils was not effective. A similar process was applied to the production of a lipid extract of *Chlorella* enriched with DHA, which contained 20% DHA (Sugimoto et al., 2002, Biol. Pharm. Bull 25:1090-1092). In this case, the percentage of EPA was slightly greater than 3%. This process, which is associated with the one already described for enrichment with vitamin B12, is the basis for the commercial product SUPER FRESH *CHLORELLA* SV-12 from Pacific Trading Co., Ltd.

The patent families that disclose the enrichment of *Chlorella* with polyunsaturated fatty acids, which in all cases use free fatty acids or the corresponding salts thereof, are:

KR2005015233-A; KR768757-B1: Process for producing *Chlorella* containing omega-3 fatty acids, including eicosapentaenoic (EPA) and docosahexaenoic (DHA) acids, which comprises the addition EPA and DHA monoglycerides to the culture medium at the end of the fermentation process.

JP10276684-A; KR98080312-A; JP3096654-B2; KR428732-B; KR423876-B: Production of *Chlorella* containing highly unsaturated fatty acids—it comprises culturing *Chlorella* in a medium with DHA and other highly unsaturated fatty acids in the form of free acids or the corresponding salts thereof.

On the other hand, as far as the applicant is aware, there is only one reference that discloses the enrichment of a species of *Nannochloropsis* with DHA (Wacker et al., 2002, Limnol. Oceanogr. 47:1242-1248). In this reference, the freshwater species *N. limnetica* was enriched separately with pure EPA or DHA, or with a DHA-rich extract of the microalga *Isochrysis* aff. *galbana* (Clone T-ISO). This latter species contains high DHA values; however, they were very inefficiently transferred to *N. limnetica*, with a final ratio of 1 part of DHA for every 40 parts of EPA (weight:weight ratio) in the enriched biomass. Moreover, these authors clearly demonstrate the benefits of DHA enrichment in the diet of the mussel *D. polymorpha*, despite the low enrichment levels achieved using their methodology (Wacker et al., 2002, Limnol. Oceanogr. 47:1242-1248).

The crucial role of long-chain polyunsaturated fatty acids in the culture of various marine species has been extensively documented (Watanabe et al., 1983, Aquaculture 34:115-143; Izquierdo, 1996, Aquaculture Nutrition, 2: 183-191; Tocher, 2010, Aquaculture Research 41:717-732), although the presence of these fatty acids has also been identified as an essential factor in freshwater environments, which controls interactions in the nutritional chain (Müller-Navarra et al., 2000, Nature 403, 74-77).

In addition to applications in aquaculture, various species of the genus *Nannochloropsis* have been extensively studied as a source of EPA for nutritional applications in humans and animals (Sukenik, 1998, Cohen, Z. (Ed.), Chemicals from Microalgae. Taylor and Francis, London, p 41-56; Chini Zitelli et al., 1999, Journal of Biotechnology 70: 299-312), and, more recently, have received great attention due to their potential for biodiesel production (Rodolfi et al., 2008, Journal of Biotechnology 70: 299-312; Doan et al., 2011, Biomass and Bioenergy 35:2534-2544; San Pedro et al., 2013, Bioresource Technology 134:353-361).

In addition to applications in aquaculture, the different properties of EPA make it a compound of high biotechnological and pharmacological interest, hence the interest in using biomass from species of the genus *Nannochloropsis*, rich in this unsaturated fatty acid, in the field of human and animal nutrition. It has been demonstrated that the n-3 series polyunsaturated fatty acids EPA and DHA present a number of health benefits, and are effective in the treatment of cardiovascular diseases, including well-documented hypotriglycemic and anti-inflammatory effects. Similarly, several studies have suggested promising antihypertensive, anti-carcinogenic, anti-depression, anti-ageing and anti-arthritic effects. An anti-inflammatory and insulin-sensitising effect in metabolic disorders has also been disclosed. More specifically, various studies suggest that EPA may be beneficial in inflammatory processes, schizophrenia, depression, chronic fatigue syndrome, hepatic dysfunction, attention deficit hyperactivity syndrome, etc., and also improve the efficiency of chemotherapy in cancer processes (Siriwardhana et al., 2012, Se-Kwon Kim, (Eds.), Advances in Food and Nutrition Research, Academic Press, 2012, Volume 65, Pages 211-222). In animal experimentation systems, it has been demonstrated that the inclusion of EPA-rich *Nannochloropsis* biomass results in a greater proportion of DHA in the brain lipids of rat offspring, and also a better appearance and a greater DHA content in the eggs of hens fed with biomass from this species (Sukenik, 1999, Cohen, Z. (Ed.), Chemicals from Microalgae. Taylor and Francis, London, p 41-56).

If EPA-rich microalgal biomass is of great interest for application in the fields of aquaculture, animal breeding and the treatment of diseases in humans, arising from the aforementioned properties, obtaining biomass that is also enriched with DHA is of even greater interest. DHA is one of the main components of fish oil and, in addition to being essential for the development of marine species, it is very abundant in the brain phospholipids of mammals. It has been suggested that DHA is necessary for neuronal development and synaptic plasticity. The DHA content in brain phospholipids is also lower in patients with Alzheimer's disease. Moreover, the high DHA content in human breast milk has been related to the development of the central nervous system in children, which has led to the recommendation of supplementing formula milks with this compound. Other possible applications of DHA include anti-carcinogenic activity, psoriasis, etc. Moreover, numerous studies suggest that DHA is an important component for maintaining and improving cerebral functions in aged animals (Sugimoto et al., 2002, Biol. Pharm. Bull 25:1090-1092). Commercially, DHA designed for use in human nutrition is produced from fish oil or the heterotrophic dinoflagellate *Crypthecodinium cohnii* (Mendes et al., 2008, Journal of Applied Phycology 21:199-214). The use of DHA from *C. cohnii* for food enrichment, particularly in the field of aquaculture, is disclosed in the patent Gladue et al., 2002, U.S. Pat. No. 6,372,460 B1. Although there exist DHA-rich microalgae, with a DHA content that may range between 10% and 20% (Volkman et al., 1989, Journal of Experimental Marine Biology and Ecology, 128: 219-240), those species with a high content of this fatty acid present low levels of EPA.

Therefore, both in the field of aquaculture and in the field of animal and human nutrition, the availability of microalgal biomass simultaneously enriched with EPA and DHA is of great interest. A product with these characteristics has not been disclosed in the literature and is not in the market; consequently, it is still a challenge to obtain a microalga simultaneously enriched with EPA and DHA.

BRIEF DESCRIPTION OF THE INVENTION

The authors of the present invention have developed an enrichment process that makes it possible to obtain microalgal biomass with a high simultaneous content of eicosapentaenoic acid (20:5 n-3) (EPA) and docosahexaenoic acid (22:6 n-3) (DHA). In particular, the microalgal biomass belongs to the genus *Nannochloropsis*.

One advantage of the invention is that the ratio between EPA and DHA is greater than 0.5 parts of DHA for every 10 parts of EPA, and a ratio of 2.4 parts of DHA for every 1 part of EPA may be achieved, the percentage of EPA being at least 10% of the total fatty acids in the biomass.

Figure 5:
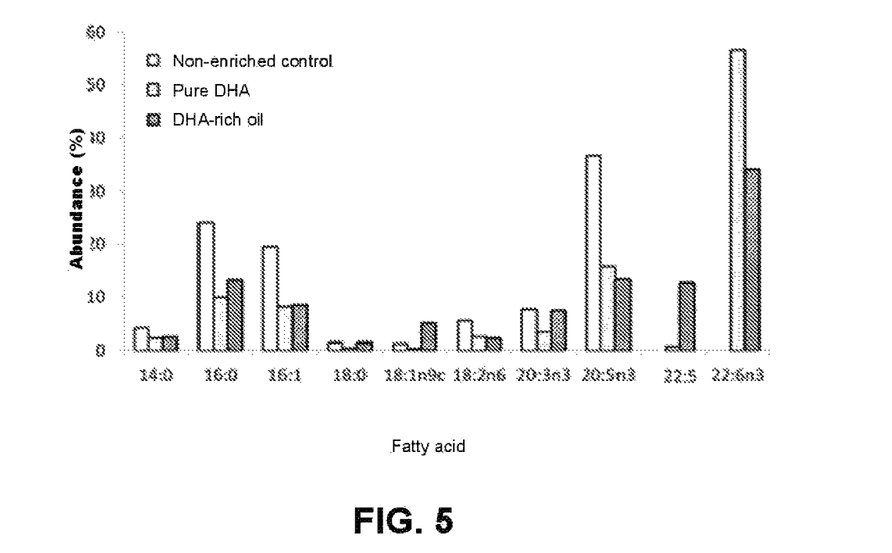
FIG. 5 shows the % of fatty acids with respect to the total in *N. limnetica* concentrates enriched for 24 hours with pure DHA or with DHA-rich oil, both at a concentration of 2.5 mg/ml and in the presence of an emulsifying agent, following the process described in EXAMPLE 2.
Figure 6:
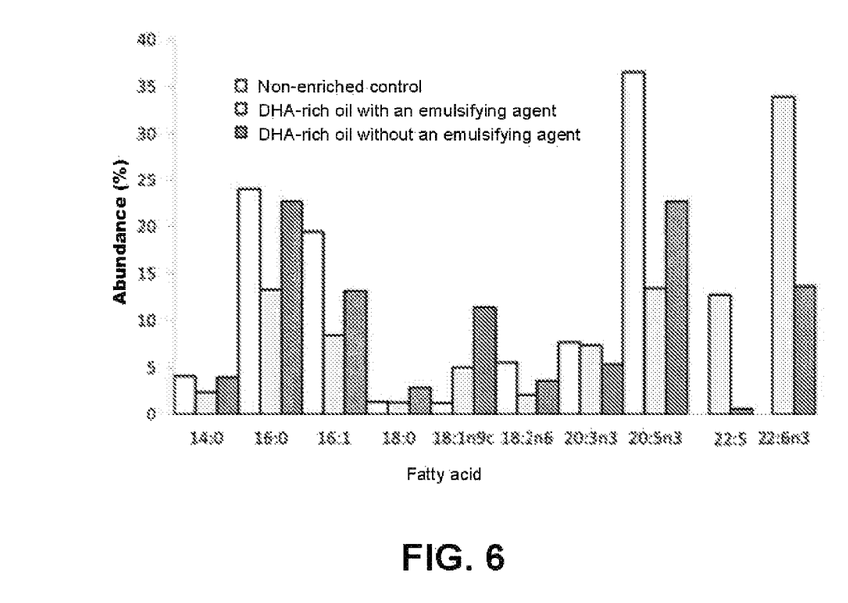
FIG. 6 shows the % of fatty acids with respect to the total in *N. limnetica* concentrates enriched with DHA-rich oil at a concentration of 2.5 mg/ml for 24 hours in the presence of an emulsifying agent and in the absence thereof, following the process described in EXAMPLE 2.

One additional advantage of the invention is that, moreover, the microalgal biomass obtained has a high content of other polyunsaturated acids, such as, for example, polyunsaturated acid 22:5, as shown in FIGS. 5 and 6, which is greater than 10% by weight with respect to the weight of the biomass concentrate.

As may be observed in the examples and the figures, when applying the process of this invention, the EPA:DHA ratio obtained is much greater than any other previously described, since the authors of the present invention obtained a ratio of up to 2.4 parts of DHA for every part of EPA in the presence of the emulsifying agent and of 0.6 parts of DHA for every part of EPA in the absence thereof.

Thus, one aspect of the invention relates to a process for enriching microalgal biomass of the genus *Nannochloropsis* with polyunsaturated acids, which comprises:

a) mixing i) a suspension of live microalgal biomass of the genus *Nannochloropsis* wherein the dry weight ratio of the microalgae ranges between 0.1% and 20% with respect to the total volume of the suspension, with ii) a solution or an emulsion of fatty acids that comprises a quantity of docosahexaenoic acid greater than 5% by weight with respect to the total fatty acids, and b) allowing the resulting mixture to rest for at least 24 hours.

Another aspect of the invention relates to a microalgal biomass of the genus *Nannochloropsis*, characterised in that it comprises eicosapentaenoic acid (20:5 n-3) (EPA) and docosahexaenoic acid (22:6 n-3) (DHA) with a DHA weight ratio equal to or greater than 1 part of DHA for every 10 parts of EPA, and contains a proportion of eicosapentaenoic acid (20:5 n-3) (EPA) of at least 10% with respect to the total fatty acids in the biomass.

Another aspect of the invention relates to a microalgal biomass of the genus *Nannochloropsis*, which may be obtained by means of the process described above.

Another aspect of the invention relates to the use of the microalgal biomass of the genus *Nannochloropsis* described above, which has applications in aquaculture, in animal breeding, for the improvement of the fatty acid profile of consumer products (meat, eggs, milk, etc.), and in the cosmetics sector.

Another aspect of the invention relates to the use of the microalgal biomass of the genus *Nannochloropsis* described above for the preparation of a nutraceutical product. In particular, the nutraceutical product of the present invention may be applied in cases of infertility, nervous system diseases and circulatory system diseases, in addition to serving as a food supplement.

The present invention is characterised by the fact that the process uses a concentrated biomass instead of diluted cultures, by the biomass exposure times and conditions, by the possibility to use an emulsifying agent, by the modification of the ratio between the biomass and the lipid concentration, as well as by the use of an oil as the source of fatty acids.

DESCRIPTION OF THE FIGURES

In order to supplement the description being made, and to contribute to a better understanding of the characteristics of the invention, according to a preferred embodiment thereof, a set of drawings is attached to said description as an integral part thereof, where the following is represented for illustrative, non-limiting purposes.

DETAILED DESCRIPTION OF THE INVENTION

One aspect of the invention relates to a process for enriching microalgal biomass of the genus *Nannochloropsis* with polyunsaturated acids, which comprises:
a) mixing i) a suspension of live microalgal biomass of the genus *Nannochloropsis*, wherein the dry weight ratio of the microalgae ranges between 0.1% and 20% with respect to the total volume of the suspension, with ii) a solution or an emulsion of fatty acids that comprises a quantity of docosahexaenoic acid greater than 5% by weight with respect to the total fatty acid content, and
b) allowing the resulting mixture to rest for at least 24 hours.

In the present invention, the microalgae of the genus *Nannochloropsis* comprise both freshwater species, such as, for example, *Nannochloropsis limnetica*, and marine water species, such as, for example, *Nannochloropsis gaditana*; moreover, it also comprises species of the same genus such as, for example, *Nannochloropsis atomus, N. coccoides, N. maculate, N. oculata, N. granulate, N. oceanica* and *N. saline*.

In another particular embodiment, the solution or emulsion of fatty acids of step a) has a concentration ranging between 10 mg/ml and 100 mg/ml. More particularly, it has a concentration of 50 mg/ml.

In a particular embodiment, the process further comprises adding a solution of emulsifying agent in step a).

In a more particular embodiment, the emulsifying agent is selected from bovine serum albumin, sodium dodecyl sulfate, polyethoxylated fatty alcohols, alkyl quaternary ammonium salts, alkyl-betaines, soy and egg lecithins, guar gum, locust bean gum, alginates, phosphoric acid, phosphate salts, sodium citrate, phosphate salts, pectin, sucrose esters, sorbitan esters, cellulose and derivatives thereof, polyethylene glycol, and mixtures thereof.

In another particular embodiment, the solution of the emulsifying agent has a concentration ranging between 10 mg/ml and 100 mg/ml. More particularly, it has a concentration of 50 mg/ml.

In another particular embodiment, the volume ratio between the fatty acid solution of step a) and ii) the solution of the emulsifying agent ranges between 1:1 and 1:4. In another particular embodiment, the ratio is 1:2.

In another particular embodiment, the dry weight ratio of the microalgae of step a) ranges between 0.8% and 15%.

In another particular embodiment, the microalgal biomass suspension and the solution or emulsion of fatty acids are mixed in step a) in a proportion ranging between 1:1 and 10:1. More particularly, the proportion is 6:1 (volume: volume).

In another particular embodiment, step b) comprises a cycle of at least 12 hours of light.

As discussed above, the invention relates to a process for enriching microalgal biomass of the genus *Nannochloropsis* with different polyunsaturated fatty acids, primarily docosahexaenoic acid (22:6 n-3, DHA). To this end, a suspension or emulsion of fatty acids is used. Said suspension or emulsion may be an oil. Thus, in a particular embodiment, the suspension or emulsion of fatty acids of step a) is a suspension or an emulsion of an oil or a mixture of oils.

In the present invention, "oil" is understood to mean a liquid that comprises a mixture of triglycerides and free fatty acids, wherein the total weight of free fatty acids is lower than 10%.

In the process of the present invention, the enrichment of the microalgal biomass of the genus *Nannochloropsis* may be performed using any oil or extract rich in long-chain polyunsaturated fatty acids, of animal or microbial origin.

In a particular embodiment, the oil is selected from oils with a percentage of DHA greater than 5% by weight with respect to the total fatty acid content, such as, for example, fish oil, such as, for example, herring oil, cod liver oil or hydrolysed derivatives. In a particular embodiment, the oil is selected from oils obtained from marine microalgae which have a DHA content greater than 5%.

In a particular embodiment, the oil is selected from herring oil, cod liver oil, oil obtained from marine microalgae, or mixtures thereof.

In a particular embodiment, the invention relates to a process for enriching microalgal biomass of the genus *Nannochloropsis* with polyunsaturated acids, which comprises:
a) mixing i) a suspension of live microalgal biomass of the genus *Nannochloropsis*, wherein the dry weight ratio of the microalgae ranges between 0.1% and 20% with respect to the total volume of the suspension, with ii) a solution or an emulsion that comprises a quantity of docosahexaenoic acid greater than 5% by weight with respect to the total fatty acid content, and with iii) a solution of an emulsifying agent, and
b) allowing the resulting mixture to rest for at least 24 hours.

In a more particular embodiment, the invention relates to a process for enriching microalgal biomass of the genus *Nannochloropsis* with polyunsaturated acids, which comprises:
a) mixing i) a suspension of live microalgal biomass of the genus *Nannochloropsis*, wherein the dry weight ratio of the microalgae ranges between 0.1% and 20% with respect to the total volume of the suspension, with ii) an oil solution or emulsion that comprises a quantity of docosahexaenoic acid greater than 5% by weight with respect to the total fatty acid content, at a concentration ranging between 10 mg/ml and 100 mg/ml, and with iii) a solution of an emulsifying agent at a concentration ranging between 10 mg/ml and 100 mg/ml, provided that solution or emulsion ii) and solution iii) are in a proportion ranging between 1:1 and 1:10, and
b) allowing the resulting mixture to rest for at least 24 hours, wherein at least 12 hours are under lighting.

In a particular embodiment, the emulsions, solutions and suspensions of the process are prepared using water, alcoholic solvents, glycolic solvents, or mixtures thereof. In a particular embodiment, ethanol is used.

Once it has been enriched, the microalgal biomass of *Nannochloropsis* may have different presentations: refrigerated or frozen concentrate, dry or lyophilised biomass, or biomass preserved by means of any other method, as well as derivative extracts.

Thus, in a particular embodiment, the invention relates to a solution, composition or lyophilisate that comprises the biomass of the invention.

The applications of the *Nannochloropsis* biomass enriched with DHA and other polyunsaturated fatty acids, preferably EPA, are: animal nutrition in the field of aquaculture and others, such as aviculture and bovine, ovine and porcine cattle, etc., without being restricted thereto, as well as nutritional supplements for pet fodder, in addition to applications in the cosmetics sector.

Another aspect of the invention relates to a nutritional supplement or functional ingredient that comprises the biomass of the present invention.

The process of the invention makes it possible to improve the DHA enrichment indices established for *Chlorella* and *N. limnetica*, whilst maintaining a high EPA enrichment. In order to establish the methodology, the following variables were studied:

- Use of concentrated biomass instead of the diluted cultures used in other methodologies. In the examples of successful enrichment shown, microalgal concentrates are used with a 1% weight/volume ratio, whereas, in the literature, the concentrate used for enrichment with pure fatty acids is 50 times more diluted (0.01% carbon weight, which is equivalent to 0.02% weight/volume (Wacker et al., 2002, Limnol. Oceanogr. 47:1242-1248).
- Modification of the biomass exposure time and conditions. In the present invention, the mixture is exposed for a minimum of 24 hours under lighting conditions, since the presence of lighting is a key factor for enrichment, whereas, in the literature, the exposure time is 4 hours, and the presence or absence of lighting is not specified.
- Modification of the ratio between the concentrate and the lipid dilution in ethanol. In the invention, ratios between the aqueous concentrate and the lipid solution in ethanol of 6:1 (one part of ethanol solution for every six parts of aqueous microalgal concentrate) are used, whereas, in the literature, the proportions of ethanol solution are much lower (100:1, i.e. 1 part of ethanol for every 100 parts of aqueous microalgal concentrate).
- Modification of the ratio between the microalgal biomass and the lipid concentration. Enrichments with an oil concentration of 2.5 mg per milliliter of mixture are obtained, whereas, in the literature, 0.025 mg of lipids per milliliter of mixture are used (Wacker et al., 2002, Limnol. Oceanogr. 47:1242-1248).
- Modification of the presence of an emulsifying agent. In the literature, an emulsifying agent at a concentration of 0.5 mg per milliliter of mixture is used. In this process, we use a concentration of 5 mg per milliliter of mixture, and enrichment is also achieved in the absence thereof.
- Modification of the source of fatty acid used. In the literature, significant enrichment is achieved using pure fatty acids or salts thereof (Hayashi et al., 2001, Biosci. Biotechnol. Biochem. 65:202-204; Wacker et al., 2002, Limnol. Oceanogr. 47:1242-1248), whereas in the present invention we use oils.

In a preferred embodiment of the invention, the process comprises the following steps:

Preparing a lipid solution in ethanol or a lipid emulsion, jointly with the emulsifying agent, which in the cited example is bovine serum albumin (BSA), which comprises the following steps:

Preparing a lipid stock solution with DHA-rich oils in ethanol,

Preparing a stock solution of an emulsifying agent in $H_2O$,

Forming an emulsion by mixing the lipid stock solution and the solution of the emulsifying agent in a 1:2 proportion, stirring until an emulsion is formed, Preparing the concentrated biomass by means of centrifugation, Enriching the concentrated biomass by adding the ethanol solution of oil or its emulsion to the concentrated biomass, allowing the mixture to be exposed to light for at least 24 hours.

Thanks to the process described, the following is achieved:

Enrichment of the *Nannochloropsis* biomass with DHA and other polyunsaturated fatty acids using oils instead of free fatty acids. The enrichment is also achieved in the absence of the emulsifying agent, although the presence thereof increases the effectiveness of the process.

Improvement of the DHA enrichment indices established for *Chlorella*, whilst maintaining a high content of EPA, which is already naturally present in the biomass of the microalgae of the genus *Nannochloropsis*, by modifying variables such as biomass concentration in the microalgal concentrate, exposure time, biomass: fatty acid ratio, lighting supply and ratio between the aqueous microalgal concentrate and the lipid solution in ethanol.

A biomass simultaneously enriched with EPA and DHA, unlike in the process described by Wacker et al. (2002, Limnol. Oceanogr. 47:1242-1248), with EPA:DHA ratios greater than 10:1 (1 part of DHA for every 10 parts of EPA) by weight being obtained in all cases and reaching 1:2.4 ratios (2.4 parts of DHA for every part of EPA).

The enrichment process is feasible for freshwater and marine species of *Nannochloropsis*.

Throughout the description and the claims, the word "comprises" and variants thereof are not intended to exclude other technical characteristics, additives, components or steps. For persons skilled in the art, other objects, advantages and characteristics of the invention will arise, partly from the description and partly from the implementation of the invention.

EXAMPLES

Example 1

In this example, conditions similar to those described in the literature for enriching *N. limnetica* were tested, using pure DHA and a fish oil with a high DHA content, and enrichment of the concentrated microalgal biomass with DHA was not achieved, which demonstrates that a simple modification of the conditions used in the literature do not allow for enrichment.

In order to perform the experiment, a concentrate of the freshwater microalga *N. limnetica* obtained by centrifugation, as described in Freire et al. (2013, Aquaculture Conference 2013: Celebrating 40 Years of Aquaculture—November, 2013, Gran Canaria (Spain)), was prepared. The cells were resuspended in distilled water, to achieve a concentration of approximately $12.3 \times 10^9$ cells/ml and a carbon concentration of 50 mg/ml (equivalent to 100 mg/ml or a 10% weight/volume ratio, considering a carbon content of 50% in the biomass). The biomass was mixed with a solution of pure DHA in ethanol at two concentrations, 250 and 2500 micrograms/ml, and fish oil with a high omega-3 content (DHA 20%-26%, EPA 7%-12%), refined EPADHAX obtained from the company Epadhax S.L.U. (Boiro, A Coruna, http://www.epadhax.eu/epadhax-omega-3-activo.php) at a concentration of 25 and 250 micrograms/ml. In all cases, the lipids were emulsified with BSA. The mixtures were incubated with the lipid emulsion for 6 hours under stirring, at a temperature of 22° C. In order to evaluate the degree of enrichment of the pastes, once the incubation period was completed, the biomass was centrifuged and washed twice with distilled water in order to eliminate all the remainders of emulsified lipids that had not been incorporated by the cells. The total lipids were extracted following the method proposed by Bligh & Dyer (1959, Can J Biochem Physiol 37: 911-917). The fatty acids were analysed by means of transmethylation with HCl and $CH_3OH$ (Sato & Murata, 1988, Beiheft Nova Hedwigia 112:391-405). The quantification and identification were performed by means of gas chromatography.

Figure 1:
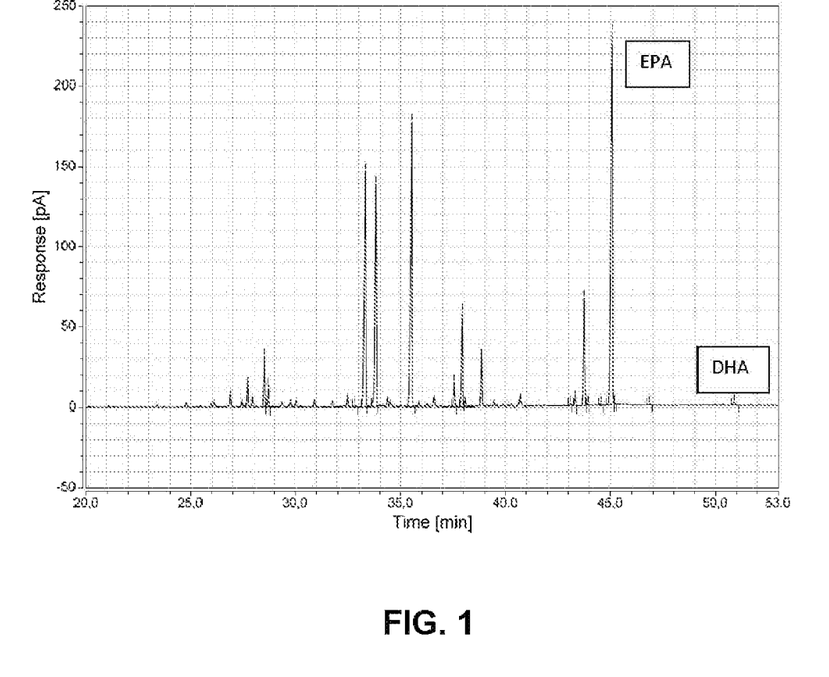
FIG. 1 shows the fatty acid profile, measured by means of gas chromatography, of a cellular concentrate of the freshwater microalga *N. limnetica* (biomass concentration, 10% weight/volume) enriched with an emulsion of pure DHA (2.5 mg/ml) for 6 hours in EXAMPLE 1. These conditions, which are similar to those described in the literature (Wacker et al., 2002) did not allow for enrichment of the biomass with DHA, since the peak pertaining to EPA, present in the biomass of all species of *Nannochloropsis*, is clearly observed at minute 45, whereas the peak pertaining to DHA, which appears at minute 51, is practically imperceptible. Enrichment with the DHA-rich oil did not achieve enrichment at any of the tested concentrations either.

The results of this first experiment were negative, as enrichment of the biomass with DHA was not achieved (FIG. 1). In this FIG. 1, corresponding to the concentrate incubated with the emulsion of pure DHA at a concentration of 250 micrograms/ml, the peak corresponding to EPA, which appears in the chromatogram at 45 minutes and is characteristic of *Nannochloropsis* species, is observed, whereas the DHA peak, which appears with an approximate retention time of 51 minutes, is practically undetectable; therefore, no enrichment was achieved.

Example 2

In this experiment, several factors, such as the biomass concentration and the exposure time, were varied with respect to the conditions described in Example 1, and incorporation of DHA was achieved, both using pure DHA and using DHA-rich oil with and without an emulsifying agent. In order to perform the experiment, a microalgal concentrate of *N. limnetica* obtained by centrifugation was used, as indicated in Example 1. This time, the cells were resuspended in distilled water in order to reach a concentration of 10 mg/ml weight/volume (1% weight:volume ratio, equivalent to approx. $1.23 \times 10^9$ cells/ml). The microalgal concentrate was mixed with DHA or DHA-rich oil at a concentration of 2.5 mg of lipid/ml, emulsified with BSA. The emulsion was prepared by mixing 50 microliters of a lipid dilution in ethanol, at a concentration of 50 mg/ml, with 100 microliters of an aqueous solution of BSA at a concentration of 50 mg/ml. The mixture was stirred in order to form the emulsion and 850 microliters of microalgal concentrate were added. In the case of the oil, the direct addition of the oil solution in ethanol (50 microliters) to the concentrate was also tested, without prior mixing with the emulsifying agent. The mixture of lipids and microalgal concentrate was incubated under stirring in the presence of light for 24 hours. In the case of pure DHA, a mixture was also incubated for 48 hours in order to test the enrichment effect during even more prolonged periods. Once the enrichment period was completed, the biomass was centrifuged and washed twice, and the fatty acid profile of the lipid extract was analysed by means of gas chromatography, following the methodology described in Example 1.

Figure 2:
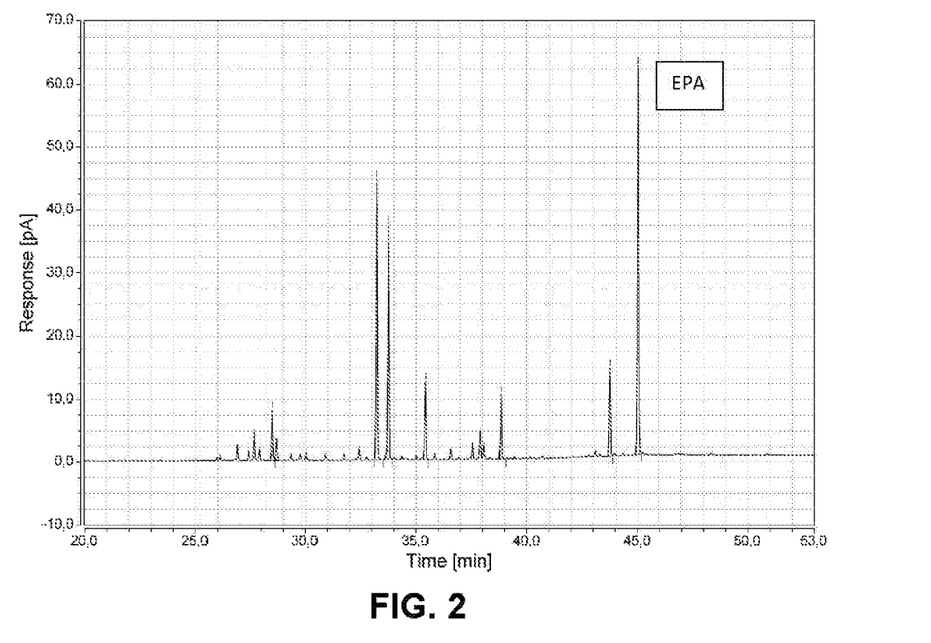
FIG. 2 shows the fatty acid profile, measured by means of gas chromatography, of a concentrate of non-enriched *N. limnetica* (biomass concentration, 1% dry weight/volume) originating from the experiment described in EXAMPLE 2, wherein only the EPA peak specific to species of *Nannochloropsis* appears.
Figure 3:
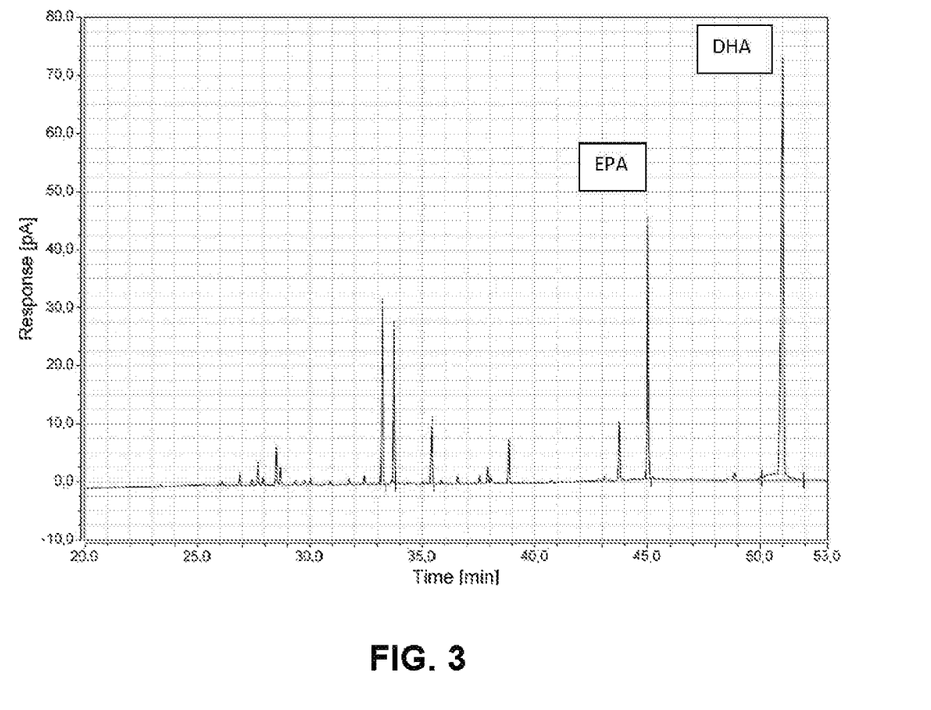
FIG. 3 shows the fatty acid profile, measured by means of gas chromatography, of a concentrate of *N. limnetica* (biomass concentration, 1% dry weight/volume) enriched with an emulsion of pure DHA (2.5 mg/ml) for 24 hours, originating from the experiment described in EXAMPLE 2. The existence of the peak corresponding to DHA is clearly observable at minute 51, and in this case it is greater than the peak corresponding to EPA, which appears at minute 45.
Figure 4:
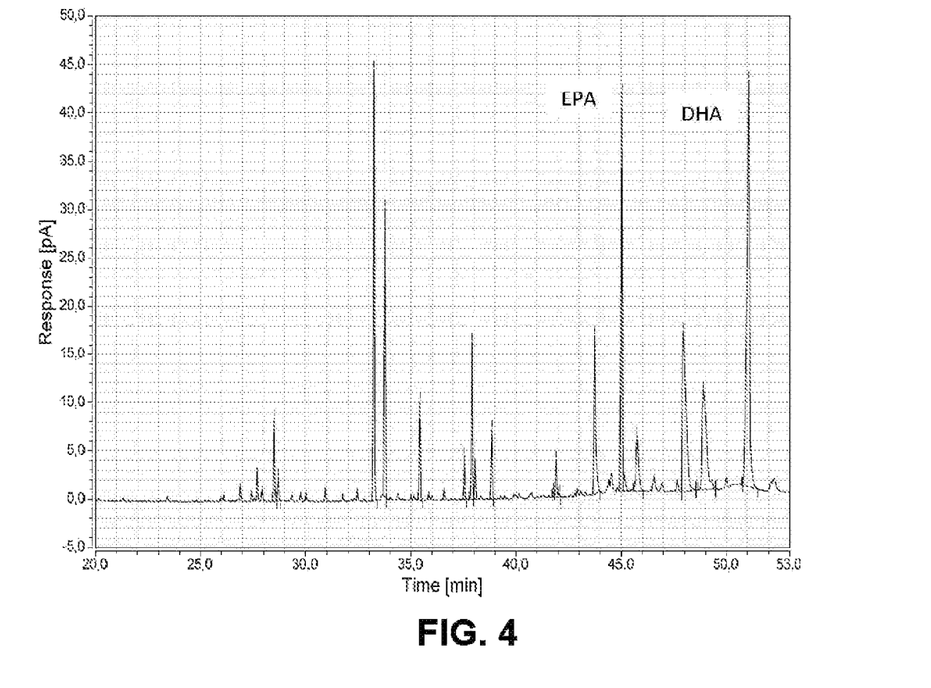
FIG. 4 shows an enrichment chromatogram of *Nannochloropsis limnetica* under the same conditions as in FIG. 3, wherein the enrichment is performed using a DHA-rich oil (content greater than 10%), where the peak corresponding to DHA is observed at minute 51, and other peaks are observed between the EPA peak (minute 45) and the DHA peak, which correspond to the incorporation of other polyunsaturated fatty acids, including acid 22:5.

FIG. 2 shows the chromatogram of non-enriched *N. limnetica* (control), wherein only EPA appears, the peak being identified at 45 minutes, and, as expected in this control concentrate, the DHA peak is absent. On the contrary, the addition of 2.5 mg/ml of the emulsion of pure DHA (FIG. 3) or the emulsion of DHA-rich oil (FIG. 4) produces the incorporation of DHA, with the appearance of a characteristic peak at 51 minutes. Moreover, when the DHA-rich oil is used, as the quantities of EPA and DHA increase, other peaks corresponding to other polyunsaturated fatty acids appear between EPA and DHA, which do not appear in the control or in the sample enriched with pure DHA.

The values obtained with the different enrichment protocols, as the % of the total fatty acids and the cellular content by weight (pg per cell), are represented in Table 1, which shows the fatty acid profile of the *N. limnetica* concentrate enriched with pure DHA for 24 and 48 hours, and with DHA-rich oil (EPADHAX) with and without an emulsifying agent (BSA in this example) for 24 hours.

TABLE 1

Fatty acid profile of the *Nannochloropsis limnetica* biomass, not enriched (control) or enriched with pure DHA and DHA-rich oil (EPADHAX) at a concentration de 2.5 mg/ml, in both cases emulsified with BSA. The enrichment was performed for 24 and 48 hours in the case of DHA, and for 24 hours in the case of the oil. In the latter case, the effect of removing BSA as an emulsifying agent (Oil 1-BSA) was also tested.

| Fatty acids | Control % | Control pg/cell | DHA 24 h % | DHA 24 h pg/cell | DHA 48 h % | DHA 48 h pg/cell |
|---|---|---|---|---|---|---|
| 14:0 | 4.08 | 0.02 | 2.17 | 0.03 | 2.49 | 0.02 |
| 16:0 | 23.99 | 0.14 | 9.89 | 0.11 | 12.16 | 0.12 |
| 16:1 | 19.46 | 0.11 | 8.19 | 0.09 | 9.29 | 0.09 |
| 18:0 | 1.38 | 0.01 | 0.42 | 0.00 | 0.48 | 0.00 |
| 18:1 n9c | 1.26 | 0.01 | 0.36 | 0.00 | 1.17 | 0.01 |
| 18:1 n9t | 0.00 | 0.00 | 0.00 | 0.00 | 0.00 | 0.00 |
| 18:2 n6 | 5.57 | 0.03 | 2.46 | 0.03 | 2.71 | 0.03 |
| 18:4 n3 | 0.00 | 0.00 | 0.00 | 0.00 | 0.00 | 0.00 |
| 20:3 n3 | 7.69 | 0.04 | 3.35 | 0.04 | 3.74 | 0.04 |
| 20:5 n3 | 36.57 | 0.21 | 15.85 | 0.18 | 17.97 | 0.18 |
| 24:0 | 0.00 | 0.00 | 0.00 | 0.00 | 0.00 | 0.00 |
| 22:5 | 0.00 | 0.00 | 0.75 | 0.01 | 0.77 | 0.01 |
| 22:6 n3 | 0.00 | 0.00 | 56.56 | 0.65 | 49.22 | 0.49 |
| EPA/DHA | — | — | 0.28 | — | 0.36 | — |

| Fatty acids | OIL 1 + BSA % | OIL 1 + BSA pg/cell | OIL 1 − BSA % | OIL 1 − BSA pg/cell |
|---|---|---|---|---|
| 14:0 | 2.41 | 0.03 | 3.99 | 0.04 |
| 16:0 | 13.26 | 0.17 | 22.65 | 0.22 |
| 16:1 | 8.44 | 0.11 | 13.20 | 0.13 |
| 18:0 | 1.31 | 0.02 | 2.90 | 0.03 |
| 18:1 n9c | 5.00 | 0.06 | 11.38 | 0.11 |
| 18:1 n9t | 0.00 | 0.00 | 0.00 | 0.00 |
| 18:2 n6 | 2.12 | 0.03 | 3.62 | 0.04 |
| 18:4 n3 | 0.00 | 0.00 | 0.00 | 0.00 |
| 20:3 n3 | 7.40 | 0.10 | 5.36 | 0.05 |
| 20:5 n3 | 13.42 | 0.17 | 22.65 | 0.22 |
| 24:0 | 0.00 | 0.00 | 0.00 | 0.00 |

TABLE 1-continued

Fatty acid profile of the *Nannochloropsis limnetica* biomass, not enriched (control) or enriched with pure DHA and DHA-rich oil (EPADHAX) at a concentration de 2.5 mg/ml, in both cases emulsified with BSA. The enrichment was performed for 24 and 48 hours in the case of DHA, and for 24 hours in the case of the oil. In the latter case, the effect of removing BSA as an emulsifying agent (Oil 1-BSA) was also tested.

| 22:5 | 12.73 | 0.16 | 0.61 | 0.01 |
| 22:6 n3 | 33.92 | 0.44 | 13.65 | 0.13 |
| EPA/DHA | 0.40 | — | 1.66 | — |

The 24-hour enrichments with pure DHA and with DHA-rich oil (EPADHAX) (Table 1, FIG. 5) show a higher percentage of DHA when the latter is added in pure form (56.6%), as compared to the polyunsaturated oil (33.9%). However, in the sample enriched with the oil (Table 1, FIG. 6), we find a high percentage of other polyunsaturated fatty acids, such as fatty acid 22:5 (12.7%). These DHA contents per cell are equivalent to 80.70 micrograms of DHA per mg of dry weight in the case of enrichment with pure DHA and to 52 micrograms of DHA per milligram of dry weight in the case of EPADHAX. These values are significantly higher than those obtained by Wacker et al. (Wacker et al., 2012, Limnol. Oceanogr. 47:1242-1248), who report about 11.6 micrograms of DHA per milligram of biomass. The optimal enrichment time was established at 24 hours, since the analysis of the samples enriched with pure DHA revealed that 48-hour enrichments did not improve the levels of EPA or DHA (Table 1).

The analysis of the fatty acid profile of the samples enriched with pure DHA show that the latter is as high as 56% of the total fatty acid content with 24 hours of enrichment, and that this value is not improved with a 48-hour enrichment (Table 1).

The presence of the emulsifying agent clearly improves the incorporation of DHA and other polyunsaturated fatty acids present in the oil (Table 1, FIG. 6), but, even in the absence of the emulsifying agent, the DHA content is 13.65% of the total fatty acid content, with an EPA/DHA ratio of 1.66 (Table 1).

Example 3

In this experiment, we tested the efficiency of the enrichment process with two different species: the freshwater species *Nannochloropsis limnetica* and the marine species *Nannochloropsis gaditana*. Cell concentrates were prepared by means of centrifugation following the methodology described in Examples 1 and 2. The *N. limnetica* and *N. gaditana* cells were resuspended in distilled water or sea water, respectively, at a concentration of 1% weight/volume. Following the process and using the concentrations described in Example 2, the enrichment was performed with an emulsion of two types of DHA-rich oils in BSA: EPADHAX oil, used in Example 2 (Oil 1), and herring oil (Menhaden Oil, Sigma, CAS 8002/50/4), with a final concentration of 2.5 mg/ml (Oil 2). The oils are characterised in that they have DHA percentages of 10%-18% in the case of EPADHAX and of 8%-15% in the case of herring oil. The free fatty acid content in Oil 1 is about 14 mg per gram of oil, whereas the values described in the literature for Oil 2 are lower, about 5.5 mg per gram. It is worth noting that, due to the natural origin of these oils, the fatty acid composition and the percentage of free fatty acids may vary between different batches. The enrichments were performed in triplicate. Once the 24 hours of exposure had elapsed, the cells were concentrated by means of centrifugation, washed twice with distilled water and analysed following the methodology described in Examples 1 and 2.

Figure 7:
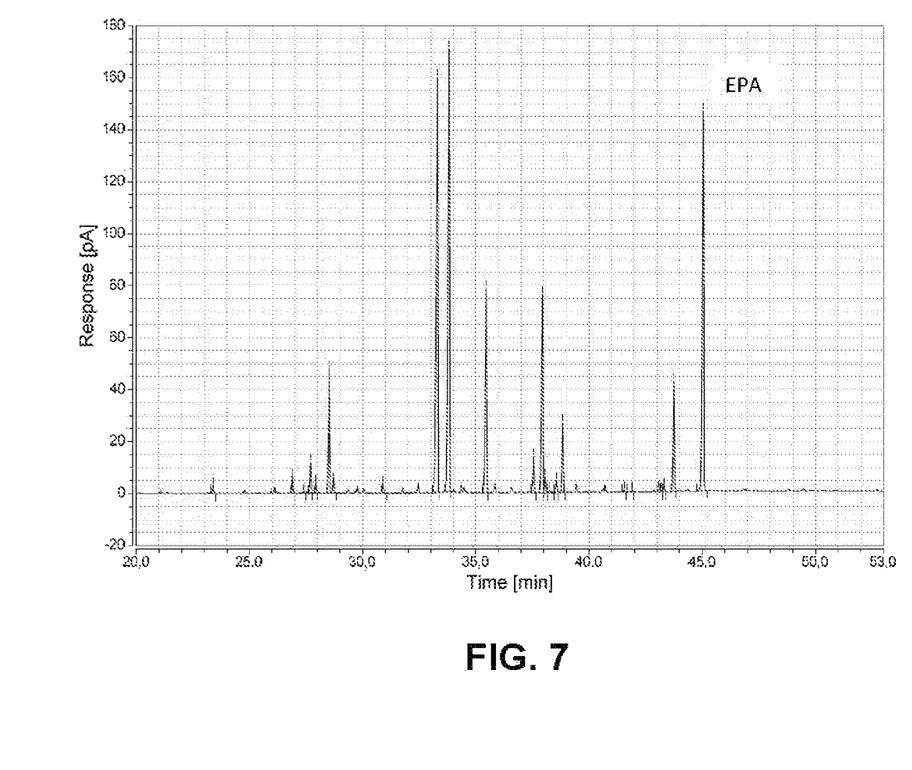
FIG. 7 shows a chromatogram of the fatty acid profile of the non-enriched marine microalga *Nannochloropsis gad-* itana (control), corresponding to the experiment described in EXAMPLE 3, where we observe the EPA peak characteristic of all species of this genus at 45 minutes. As expected in a non-enriched biomass, no peak whatsoever corresponding to DHA is observed at a retention time of 51 minutes.
Figure 8:
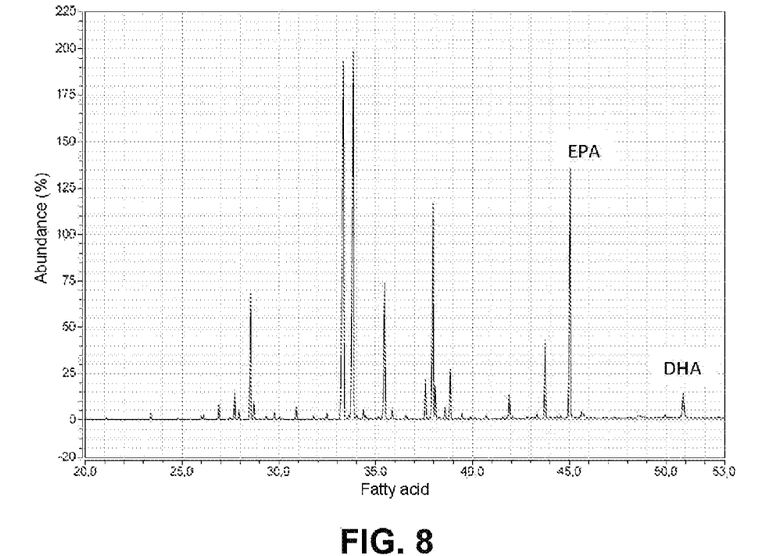
FIG. 8 shows a chromatogram of the fatty acid profile of the marine microalga *Nannochloropsis gaditana* enriched with an emulsion of DHA-rich oil (EPADHAX, which contains 10%-18% of this fatty acid), corresponding to the experiment described in EXAMPLE 3. The biomass was enriched with an oil concentration of 2.5 mg/ml for 24 hours in the presence of light. We may observe the appearance of a peak at minute 51, which corresponds to the DHA incorporated by the microalga.
Figure 9:
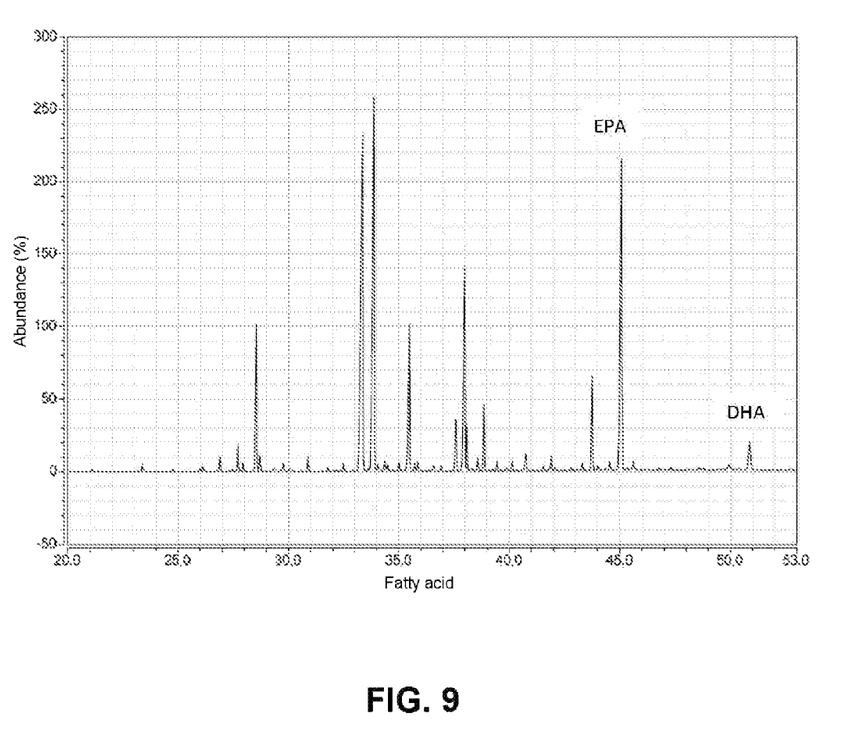
FIG. 9 shows a chromatogram of the fatty acid profile of the marine microalga *Nannochloropsis gaditana* enriched with an emulsion of DHA-rich oil (Menhaden Oil, Sigma, CAS 8002/50/4, which contains 11.9% of this fatty acid), corresponding to the experiment described in EXAMPLE 3. The biomass was enriched with an oil concentration of 2.5 mg/ml for 24 hours in the presence of light. We may observe the appearance of a peak at minute 51, which corresponds to the DHA incorporated by the microalga.

The fatty acid profile of the *N. limnetica* and *N. gaditana* cells, not enriched and enriched with the two DHA-rich oils (Oil 1 and Oil 2) are shown in Tables 2 and 3, respectively. In this experiment, DHA contents were achieved ranging between 1.5% and 2.8% of the total fatty acid content in the biomass, regardless of the species and the oil used. In all cases, there was a minimum ratio of 1 part of DHA for every 10 parts of EPA. FIGS. 7, 8 and 9 show the chromatographic profiles of *N. gaditana*, not enriched (FIG. 7) and enriched with the two types of DHA-rich oils. In these last two figures, the DHA peak at 51 minutes, resulting from the incorporation of the oils, is clearly observed.

TABLE 2

Fatty acid profile of the freshwater species *N. limnetica*, not enriched (Control) and enriched for 24 hours with two types of oils rich in polyunsaturated fatty acids added to the cellular concentrate in the form of an emulsion at a concentration of 2.5 mg/ml.

|  | Control | | Oil 1 | | Oil 2 | |
| --- | --- | --- | --- | --- | --- | --- |
|  | % | pg/cell | % | pg/cell | % | pg/cell |
| 14:0 | 6.20 | 0.01 | 4.79 ± 0.74 | 0.03 ± 0.01 | 6.01 ± 3.22 | 0.01 ± 0.01 |
| 16:0 | 24.48 | 0.04 | 4.79 ± 0.74 | 0.03 ± 0.01 | 31.01 ± 2.99 | 0.06 ± 0.01 |
| 16:1 | 25.68 | 0.04 | 18.55 ± 4.05 | 0.12 ± 0.07 | 16.14 ± 8.16 | 0.03 ± 0.03 |
| 16:2 | — | — | 2.15 ± 2.74 | 0.02 ± 0.02 | — | — |
| 18:0 | 1.65 | 0.00 | 1.97 ± 0.78 | 0.01 ± 0.00 | 2.45 ± 0.65 | 0.00 ± 0.00 |
| 18:1 n9 | 9.80 | 0.01 | 9.07 ± 5.63 | 0.06 ± 0.05 | 12.86 ± 2.32 | 0.03 ± 0.00 |
| 18:2 n6 | 2.99 | 0.00 | 2.05 ± 0.03 | 0.01 ± 0.01 | 2.87 ± 0.41 | 0.01 ± 0.00 |
| 20:3 n3 | 4.93 | 0.01 | 2.76 ± 0.61 | 0.02 ± 0.01 | 4.20 ± 0.66 | 0.01 ± 0.00 |
| 20:5 n3 (EPA) | 21.18 | 0.03 | 10.43 ± 3.04 | 0.06 ± 0.03 | 18.65 ± 3.06 | 0.04 ± 0.00 |
| 22:6 n3 (DHA) | — | — | 1.54 ± 1.05 | 0.01 ± 0.01 | 1.84 ± 0.69 | 0.00 ± 0.00 |
| EPA/DHA | — | — | 6.77 | — | 10.14 | — |

TABLE 3

Fatty acid profile of the freshwater species *N. gaditana*, not enriched (Control) and enriched for 24 hours with two types of oils rich in polyunsaturated fatty acids added to the cellular concentrate in the form of an emulsion at a concentration of 2.5 mg/ml.

|  | Control | | Oil 1 | | Oil 2 | |
|---|---|---|---|---|---|---|
|  | % | pg/cell | % | pg/cell | % | pg/cell |
| 14:0 | 4.08 | 0.02 | 6.17 ± 1.24 | 0.03 ± 0.02 | 6.05 ± 3.16 | 0.07 ± 0.05 |
| 16:0 | 23.99 | 0.14 | 29.02 ± 5.26 | 0.12 ± 0.06 | 31.54 ± 3.73 | 0.50 ± 0.37 |
| 16:1 | 19.46 | 0.11 | 14.02 ± 2.03 | 0.05 ± 0.02 | 16.29 ± 7.98 | 0.24 ± 0.17 |
| 18:0 | 1.38 | 0.01 | 2.81 ± 0.67 | 0.01 ± 0.00 | 2.50 ± 0.71 | 0.04 ± 0.03 |
| 18:1 n9 | 0.00 | 0.00 | 12.58 ± 1.79 | 0.05 ± 0.03 | 11.54 ± 1.50 | 0.17 ± 0.11 |
| 18:2 n6 | 5.57 | 0.03 | 3.12 ± 0.45 | 0.01 ± 0.01 | 2.92 ± 0.50 | 0.05 ± 0.04 |
| 20:1n9 | 0.00 | 0.00 | 1.51 ± 0.54 | 0.01 ± 0.00 | 0.58 ± 0.22 | 0.01 ± 0.01 |
| 20:3 n3 | 7.69 | 0.04 | 4.20 ± 0.86 | 0.02 ± 0.01 | 4.27 ± 0.79 | 0.07 ± 0.06 |
| 20:5 n3 (EPA) | 36.57 | 0.21 | 21.23 ± 6.60 | 0.09 ± 0.04 | 19.00 ± 3.65 | 0.31 ± 0.26 |
| 22:6 n3 (DHA) | 0.00 | 0.00 | 2.80 ± 1.14 | 0.01 ± 0.00 | 1.88 ± 0.75 | 0.03 ± 0.03 |
| EPA/DHA | — | — | 7.59 | — | 10.11 | — |

As a result of all the experiments shown, it is considered that a preferred, albeit non-limiting, process for enriching microalgal biomass of the genus *Nannochloropsis* with different fatty acids, primarily EPA and DHA, comprises the following steps:

Preparing a suspension of lipids or fatty acids in ethanol, or an emulsion of lipids or fatty acids+emulsifying agent (BSA, bovine serum albumin, or another), which, in turn, comprises:

Preparing a stock solution of lipids (which may preferably be EpaDhax$^{150}$ or DHA, Sigma D-2534, or another DHA-rich oil) in ethanol, at a concentration of 50 µg/µl.

Preparing a stock solution of BSA, which may preferably be Sigma A4503, or another emulsifying agent, in distilled $H_2O$, at a concentration of 50 mg/ml.

Preparing a master batch of lipids/pure fatty acids and BSA in a 1:2 proportion, and stirring until the emulsion is formed.

Preparing the biomass concentrate by means of centrifugation or another concentration process, such as, for example, sedimentation, flocculation, tangential filtration, etc., to obtain a final concentration of 10 mg/ml or greater, and adding the previously prepared emulsion thereto. The process may be performed with different biomass concentrations.

Enriching the biomass concentrate by the direct addition of the stock solution of lipids in ethanol or the emulsion of lipids+emulsifying agent (BSA or another) to the microalgal concentrate.

Allowing the mixture to rest under constant stirring for 24 hours in the presence of light.

In another possible embodiment, 150 µl of emulsion (lipids+emulsifying agent) may be added to 850 µl of microalgal concentrate, which represents an approximate proportion of 1:6, or any volumetric combination that maintains this proportion.

In another possible embodiment, 50 µl of a lipid solution in ethanol may be added to 950 µl of microalgal concentrate, which represents an approximate proportion of 1:20, or any volumetric combination that maintains this proportion.

The time during which the mixture is under constant stirring may be a cycle with 12 h under lighting and 12 h in the dark.

The process described and the assays performed demonstrate that the application of the conditions described in the literature is not effective to obtain enrichment in the concentrated microalgal suspensions, regardless of the source of fatty acid used, and that this enrichment may only be achieved under the conditions and with the compounds described in the invention.

Having sufficiently described the nature of the present invention, as well as the way to implement it, we state that, within its essentiality, it may be implemented in other embodiments that may differ in some details from the one described as an example, and which will equally receive the protection being requested, provided that they do not alter, change or modify the fundamental principle thereof.

REFERENCES

Ahn, Y. J., Kim, G. J., Kim, J. E., Kim, Y. H., Ko, M. S. Yun, S. Y. 2005. Process for producing *Chlorella* containing omega-3 fatty acids including eicosapentaenoic acid (EPA) and docosahexaenoic acid (DHA), comprises adding EPA and DHA monoglycerides to the culture medium at the end of fermentation. KR2005015233-A; KR768757-61.

Aragao, C., Conceição, L. E. C., Dinis, M. T., Fyhn, H.-J. 2004. Amino acid pools of rotifers and Artemia under different conditions: nutritional implications for fish larvae. Aquaculture 234: 429-445.

Basen, T., Rothhaupt, K.-O., Martin-Creuzburg, D. 2012. Absence of sterols constrains food quality of cyanobacteria for an invasive freshwater bivalve. Oecologia 170: 57-64.

Bentley, C. D., Carroll, P. M., Watanabe, W. O. 2008. Intensive rotifer culture in a pilot-scale continuous recirculating system using nonviable microalgae and an ammonia neutralizer. J World Aquac Soc 39:625-635.

Bligh, E. G., Dyer, W. J. 1959. A rapid method of total lipid extraction and purification. Can J Biochem Physiol 37: 911-917.

Chini Zittelli, G. Lavista, F., Bastianini, A., Rodolfi, L., Vincenzini, M., Tredici, M. R. 1999. Production of eicosapentaenoic acid by *Nannochloropsis* sp. cultures in outdoor tubular photobioreactors. Journal of Biotechnology 70: 299-312.

*CHLORELLA* KOGYO CO. LTD. 1999. Production of *Chlorella* containing highly unsaturated fatty acids— comprises culture of *Chlorella* in medium containing DHA and other highly unsaturated fatty acids in free acid or salt form. JP10276684-A; KR98080312-A; JP3096654-B2; KR428732-B; KR423876-B.

Doan, T. T. Y., Sivaloganathan, B., Obbard, J. P. 2011. Screening of marine microalgae for biodiesel feedstock. Biomass and Bioenergy 35: 2534-2544.

Ferreira, M., Coitinho, P., Seixas, P., Fabregas, J., Otero, A. 2009. Enriching rotifers with "premium" microalgae. *Nannochloropsis gaditana*. Mar Biotechnol 11:585-595.

Freire, I., Cortina, A., Barreiro, P., Llamas B., Otero, A. 2013. *Nannochloropsis limnetica*: a new freshwater microalgal species for marine aquaculture. Aquaculture Conference 2013: Celebrating 40 Years of Aquaculture—November, 2013, Gran Canaria (Spain).

Gladue, R. M., Behrens, P. W. 2002. DHA-containing nutritional compositions and methods for their production. U.S. Pat. No. 6,372,460B1.

Hayashi, M., Yukino, T., Maruyama, I., Kido, S., Kitaoka, S. 2001. Uptake and accumulation of exogenous docosahexaenoic acid by *Chlorella*. Biosci. Biotechnol. Biochem. 65:202-204.

Hibberd, D. J. 1981. Notes of the taxonomy and nomenclatures of the algal clases Eustigmatophyceae and Trbophyceae (synom Xanthophyceae). Bot J Linnean Society 82:93-119.

Hibberd, D. J., Leedale, G. F. 1972. Observations on the cytology and ultrastructure of the new algal class, Eustigmatophyceae. Annals of Botany 36:49-71.

Hirayama, K., Nakamura, K. 1976. Fundamental studies on the physiology of rotifers in mass culture—V. Dry *Chlorella* powder as a food for rotifers. Aquaculture 8:301-307.

Izquierdo, M. S. 1996. Essential fatty acid requirements of cultured marine fish larvae. Aquaculture Nutrition, 2: 183-191.

Jeffrey, S. W., Vesk, M. 1997. Introduction to marine phytoplankton and their pigment signatures. In: Phytoplankton pigments in oceanography. S. W. Jeffrey, R. F. C. Mantoura, S. W. Wright (Eds.). UNESCO Publishing Paris, pp 37-84.

Kobayashi, T., Nagase, T., Hino, A., Takeuchi, T. 2008. Effect of combination feeding of *Nannochloropsis* and freshwater *Chlorella* on the fatty acid composition of rotifer *Brachionus* plicatilis in a continuous culture. Fisheries Sci 74:649-656.

Koiso, M., Yoshikawa, M., Kuwada, H., Hagiwara, A. 2009. Effect of maternal diet on survival and life history parameters of next generations in the rotifers *Brachionus plicatilis* sp. complex. Nippon Suisan Gakk 75:828-833.

Krienitz, L., Hepperle, D., Stich, H.-B. Weiler, W. 2000. *Nannochloropsis limnetica* (Eustigmatophyceae), a new species of picoplankton from freshwater. Phycologia 39:219-227.

Krienitz, L., Manfred, W. 2006. The high content of polyunsaturated fatty acids in *Nannochloropsis limnetica* (Eustigmatophyceae) and its implication for food web interactions, freshwater aquacultulture and biotechnology. Limnologia 36:204-210.

Lubian, L. M., Establier, R. 1982. Estudio comparativo de la composición de pigmentos de varias cepas de *Nannochloropsis* (Eustigmatophyceae). Investigación Pesquera 46:379-389.

Luzbens, E., Gibson, O., Zmora, O., Sukenik, A. 1995. Potential advantages of frozen algae (*Nannochloropsis* sp.) for rotifer (*Brachionus plicatilis*) culture. Aquaculture 133:295-309.

Maruyama, I., Nakamura, T., Matsubayashi, T., Ando, Y., Maeda, T. 1986. Identification of the alga known as "marine *Chlorella*" as a member of the Eustigmatophyceae. Jap. J. Phycol. 34:319-325.

Maruyama, I., Ando, Y., Maeda, T., Hirayama, K. 1989. Uptake of vitamin B12 by various strains of unicellular algae *Chlorella*. Nippon Suisan Gakkaishi 55:1785-1790.

Maruyama, I., Hirayama, K. 1993. The culture of the rotifer *Brachionus* plicatilis with *Chlorella vulgaris* containing Vitamin B12 in its cells. Journal of the World Aquaculture Society 24:194-198.

Maruyama, I., Nakao, I., Shigueno, Y., Ando, Y., Hirayama, K. 1997. Application of unicellular algae *Chlorella vulgaris* for the mass culture of marine rotifer *Brachionus*. Hydrobiologia 358: 133-138.

Mendes, A., Reis, A., Vasconcelos, R., Guerra, P., Lopes da Silva, T. 2008. *Crypthecodinium cohnii* with emphasis on DHA production: a review. Journal of Applied Phycology 21:199-214.

Müller-Navarra, D. C., Brett, M. T., Liston, A. M., and Goldman, C. R. 2000. A highly unsaturated fatty acid predicts carbon transfer between primary producers and consumers. Nature 403:74-77.

Nuria Navarro, N., Yúfera, M., García-Gallego, M. 2001. Use of freeze-dried microalgae for rearing gilthead seabream, *Sparus aurata* L., larvae. II. Biochemical composition. Hydrobiologia 452: 69-77.

Rodolfi, L., Chini Zitelli, G., Bassi, N., Padovani, G., Biondi, N., Bonini, G., Tredici, M. R. 2008. Microalgae for oil: strain selection, induction of lipids synthesis and outdoor mass cultivation in a low-cost photobioreactor. Biotechnol Bioeng 102:100-112.

San Pedro, A., González-López, C. V., Acién, F. G., Molina-Grima, E. 2013. Marine microalgae selection and culture conditions optimization for biodiesel production. Bioresource Technology 134:353-361.

Santos, L. M. 1996. The Eustigmatophyceae: actual knowledge and research perspectives. Beiheft Nova Hedwigia 112:391-405.

Sato N., Murata. 1988. Membrane lipids. In: Packer L., Glazer A. N. (Eds.). Methods Enzimol. Vol. 167. Academic Press, New York, 251-259.

Siriwardhana, N., Kalupahana, N. S., Moustaid-Moussa, N. 2012. Health Benefits of n-3 Polyunsaturated Fatty Acids: Eicosapentaenoic Acid and Docosahexaenoic Acid, In: Se-Kwon Kim (Ed.), Advances in Food and Nutrition Research, Academic Press, 2012, Volume 65, Pages 211-222.

Srivastava, A., Hamre, K., Stoss, J., Chakrabarti, R., Tonheim, S. K. 2006. Protein content and amino acid composition of the live feed rotifer (*Brachionus plicatilis*): with emphasis on the water soluble fraction. Aquaculture 254:534-543

Sugimoto, Y., Taga, C., Nishiga, M., Fujiwara, M., Konishi, F., Tanaka, K., Kamei, C. 2002. Effect of docosahexaenoic acid-fortified *Chlorella* vulgaris strain CK22 on the radial maze performance in aged mice. Biol. Pharm. Bull 25:1090-1092.

Sukenik, A. 1999. Production of eicosapentaenoic acid by the marine eustigmatophyte *Nannochloropsis* sp. In: Cohen, Z. (Ed.), Chemicals from Microalgae. Taylor and Francis, London, p 41-56.

Sukenik, A., Zmora, O., Carmeli, Y. 1993. Biochemical quality of marine unicellular algae with special emphasis on lipid composition. II. *Nannochloropsis* sp. Aquaculture 117:313-326.

Tocher, D. R. 2010. Fatty acid requirements on ontonegy of marine and freshwater fish. Aquaculture research 41:717-732.

Volkman, J. K., Jeffrey, S. W., Nichols, P. D., Rogers, G. I., Garland, C. D. 1989. Fatty acid and lipid composition of 10 species of microalgae used in mariculture. Journal of Experimental Marine Biology and Ecology, 128: 219-240.

Wacker, A., Becher, P., von Elert, E. 2002. Food quality effects of unsaturated fatty acids on larvae of the zebra mussel *Dreissena polymorpha*. Limnol. Oceanogr. 47:1242-1248.

Wacker, A., Martin-Creuzburg, M. 2007. Allocation of essential lipids in *Daphnia magna* during exposure to poor food quality. Functional ecology 21:738-747.

Wacker, A., von Elert, E. 2003. Food quality controls reproduction of the zebra mussel (*Dreissena polymorpha*). Oecologia 135:332-338.

Watanabe, T., Kitayama, C., Fujita, S. 1983. Nutritional values of live organisms used in Japan for mass propagation of fish: a review. Aquaculture 34:115-143.

Whittle, S. J., Casselton, P. J. 1975. The chloroplast pigments of the algal classes Eustigmatophyceae and Xantophyceae. I. Eustigmatophyceae. British Phycological Journal 10:179-191.

Yoshimura, K., Tanaka, K., Yoshimatsu, T. 2003. A novel culture system for the ultra-high-density production of the rotifer, *Brachionus rotundiformis*—a preliminary report. Aquaculture 227:165-172.

The invention claimed is:

1. A process for enriching microalgal biomass of the genus *Nannochloropsis* with polyunsaturated fatty acids, which comprises:
   a) mixing i) a suspension of live microalgal biomass of the genus *Nannochloropsis*, wherein the dry weight ratio of the microalgae ranges between 0.1% and 20% with respect to the total volume of the suspension, with ii) a solution or an emulsion of fatty acids that comprises a quantity of docosahexaenoic acid greater than 5% by weight with respect to the total fatty acid content, with iii) a solution of an emulsifying agent and
   b) allowing the resulting mixture to rest for at least 24 hours, wherein the solution or emulsion of fatty acids of step a) has a concentration ranging between 10 mg/ml and 100 mg/ml.

2. The process according to claim 1, wherein the emulsifying agent is selected from bovine serum albumin, sodium dodecyl sulfate, polyethoxylated fatty alcohols, alkyl quaternary ammonium salts, alkyl-betaines, soy and egg lecithins, guar gum, locust bean gum, alginates, phosphoric acid, phosphate salts, sodium citrate, phosphate salts, pectin, sucrose esters, sorbitan esters, cellulose and derivatives thereof, polyethylene glycol, and mixtures thereof.

3. The process according to claim 1, wherein the solution of the emulsifying agent has a concentration ranging between 10 mg/ml and 100 mg/ml.

4. The process according to claim 3, wherein the ratio between the solution or emulsion of fatty acids ii) of step a) and the solution of the emulsifying agent ranges between 1:1 and 1:4.

5. A process for enriching microalgal biomass of the genus *Nannocloropsis* with polyunsaturated fatty acids, which comprises:
   a) mixing i) a suspension of live microalgal biomass of the genus *Nannochloropsis*, wherein the dry weight ratio of the microalgae ranges between 0.1% and 20% with respect to the total volume of the suspension, with ii) an oil solution or emulsion that comprises a quantity of docosahexaenoic acid greater than 5% by weight with respect to the total fatty acid content, at a concentration ranging between 10 mg/ml and 100 mg/ml, and with iii) a solution of an emulsifying agent at a concentration ranging between 10 mg/ml and 100 mg/ml, provided that solution or emulsion ii) and solution iii) are in a proportion ranging between 1:1 and 1:10, and
   b) allowing the resulting mixture to rest for at least 24 hours, wherein at least 12 hours are under lighting.

6. The process according to claim 5, wherein:
   the oil emulsion or solution is a lipid solution in ethanol, at a concentration of 50 µg/µl, wherein the lipid solution may be EpaDhax[150] or DHA, Sigma D-2534, or another DHA-rich oil;
   the solution of the emulsifying agent is a stock solution of BSA; and
   the solution of lipids and the stock solution of BSA are mixed in a 1:2 proportion, by stirring until the emulsion is formed.

7. The process according to claim 5, wherein the suspension of live microalgal biomass is obtained by means of centrifugation or another concentration process, such as, for example, sedimentation, flocculation or tangential filtration.

* * * * *